United States Patent
Sung et al.

(10) Patent No.: US 9,228,202 B2
(45) Date of Patent: Jan. 5, 2016

(54) INTRACELLULAR VIRAL VECTOR DELIVERY METHOD EMPLOYING IRON ION/VIRAL VECTOR COMPOSITE

(75) Inventors: Young Chul Sung, Seoul (KR); Sang Hoon Park, Anyang-si (KR); Ki Seok Park, Pohang-si (KR)

(73) Assignees: POSTECH ACADEMY-INDUSTRY FOUNDATION, Pohang-si, Gyeongsangbuk (KR); BIOD CO., LTD., Pohang-si, Gyeongsangbuk (KR)

( * ) Notice: Subject to any disclaimer, the term of this patent is extended or adjusted under 35 U.S.C. 154(b) by 440 days.

(21) Appl. No.: 13/499,101

(22) PCT Filed: Sep. 28, 2010

(86) PCT No.: PCT/KR2010/006577
§ 371 (c)(1),
(2), (4) Date: Mar. 29, 2012

(87) PCT Pub. No.: WO2011/040738
PCT Pub. Date: Apr. 7, 2011

(65) Prior Publication Data
US 2012/0183573 A1    Jul. 19, 2012

(30) Foreign Application Priority Data
Oct. 1, 2009   (KR) .................. 10-2009-0093832

(51) Int. Cl.
*C12N 15/86* (2006.01)
*C12N 15/63* (2006.01)
*C12N 15/864* (2006.01)
(Continued)

(52) U.S. Cl.
CPC ............ *C12N 15/86* (2013.01); *C12N 15/63* (2013.01); *C12N 15/00* (2013.01); *C12N 15/861* (2013.01); *C12N 15/863* (2013.01); *C12N 15/864* (2013.01); *C12N 15/867* (2013.01); *C12N 15/8636* (2013.01);
(Continued)

(58) Field of Classification Search
None
See application file for complete search history.

(56) References Cited

U.S. PATENT DOCUMENTS 6,949,379 B2    9/2005 Ramachandra
2005/0142111 A1    6/2005 Wu et al.

FOREIGN PATENT DOCUMENTS

JP          08-308573         11/1996
JP    WO 2005/095621 A1 *    10/2005
(Continued)

OTHER PUBLICATIONS

Wang, et al. Coxsackievirus and adenovirus receptor expression in non-malignant lung tissues and clinical lung cancers. J. Mol. Hist. 2006; 37(3-4): 153-160.*

(Continued)

*Primary Examiner* — Benjamin P Blumel
*Assistant Examiner* — Stuart W Snyder
(74) *Attorney, Agent, or Firm* — Lucas & Mercanti, LLP (57) ABSTRACT

The present invention relates to an intracellular viral vector delivery method employing an iron ion/viral vector composite. The iron ion/viral vector composite according to the present invention is not dependent on the expression of CAR and so improves the efficiency of delivery of viral vectors and gene expression in cells of diverse types, and has an outstanding virus-neutralizing antibody escape performance, exhibits little cytotoxicity and is outstandingly stable even when subjected to iron ion processing at low concentration, and hence can be used to advantage in recombinant viral vaccine compositions.

5 Claims, 5 Drawing Sheets

(51) Int. Cl.
- *C12N 15/861* (2006.01)
- *C12N 15/867* (2006.01)
- *C12N 15/00* (2006.01)
- *C12N 15/863* (2006.01)

(52) U.S. Cl.
CPC ........... *C12N 2710/10343* (2013.01); *C12N 2710/10345* (2013.01); *C12N 2810/10* (2013.01)

(56) References Cited

FOREIGN PATENT DOCUMENTS

| KR | 1020050020790 | 3/2005 |
|---|---|---|
| KR | 1020080031532 | 4/2008 |

OTHER PUBLICATIONS

Bland, J. Investigation Into the Crystal and Magnetic Structure of Magnetite (Fe3O4) Using Mössbauer Spectroscopy. University of Liverpool Masters of Physics Project. 1998.*

Shimbo, et al. (Development of a transferrin receptor-targeting HVJ-E vector. BBRC, 2007; 363: 423-428).*

Kay et al. Viral vectors for gene therapy: the art of turning infectious agents into vehicles of therapeutics. Nat Med. 2001; 7(1): 33-40.*

Zhang and Godbey, Viral vectors for gene delivery in tissue engineering. Adv. Drug Del. Rev. 2006; 58: 515-534.*

Bouard et al. Viral vectors: from virology to transgene expression. Br. J. Pharmacol. 2009; 157: 153-165.*

Cevher et al. "Gene Delivery Systems: Recent Progress in Viral and Non-Viral Therapy" in "Recent Advances in Novel Drug Carrier Systems" E. A.D. Sezer. InTech, 2012; 437-470.*

Nayerossadat et al. Viral and nonviral delivery systems for gene delivery. Adv. Biomed. Res. 2012; 1(27): 1-23.*

Roy, et al., "Calcium phosphate nanoparticles as novel non-viral vectors for targeted gene delivery", Int. J. Pharmaceutics, vol. 230, pp. 25-33, Dec. 31, 2003.

Ye, et al., "Tagging retrovirus vectors with a metal binding peptide and one-step purification by immobilized metal affinity chromatography", J. Virology, vol. 78, No. 18, pp. 9820-9827, Sep. 31, 2004.

Duffy, et al., "Purification of adenovirus and adeno-associated virus: comparison of novel membrane-based technology to conventional techniques", Gene Therapy, vol. 12, pp. S62-S72, Dec. 31, 2005.

\* cited by examiner

INTRACELLULAR VIRAL VECTOR DELIVERY METHOD EMPLOYING IRON ION/VIRAL VECTOR COMPOSITE

CROSS-REFERENCE TO RELATED APPLICATIONS

This application is a 371 of PCT/KR2010/006577, filed Sep. 28, 2010, which claims the benefit of Korean Patent Application No. 10-2009-0093832, filed Oct. 1, 2009, the contents of each of which are incorporated herein by reference.

TECHNICAL FIELD

The present invention relates to a method for viral vector-mediated gene delivery into cells, using an iron ion/viral vector composite.

BACKGROUND ART

There are many different methods for gene delivery, including the use of DNA, RNA or viral vectors. Viral vectors are widely used to date because when introduced into host cells by viral vectors, genes can be stably expressed for a long period of time in the host cells (Cancer Gene Ther. 1994; 1:51-64). Of the viruses used for mediating gene delivery, however, retroviruses and lentiviruses have problems in clinical application because they may cause the gene of interest to be incorporated into the chromosome of the host cells, which may result in a mutation. In contrast, when adenoviruses are manipulated so as not to be incorporated into the chromosome of the host cell, the recombinant adenoviruses may be free from association with oncogenesis and thus be safe. In addition, E1/E3-deleted recombinant adenovirus is more safe because it is not only replication deficient due to E1 deletion, but also does not alter the immune response of the host cells due to E3 deletion. In addition, an adenovirus has additional advantages making it suitable for use as a vector (Curr Opin Genet Dev. 1993; 3:499-503). That is, an adenovirus can accommodate a gene insert as large as up to 8 kb and express it at a high concentration. Moreover, adenovirus can infect many different cells. Although epithelial cells of the eye, the respiratory tract, the intestine and the urinary tract are the most susceptible to adenoviral infection, an adenovirus can infect the liver, the muscles and the heart of mice as well as nerve cells, hepatic cells, lymphocytes, macrophages, endothelial cells, and fibrocytes.

However, because the intracellular uptake of the adenovirus particle is primarily mediated by the coxsackievirus and adenovirus receptor (CAR), it is very difficult to apply an adenovirus to the effective introduction of genes into cells that have a low level of CAR, such as cancer cells and stem cells (J Clin Invest. 1997; 100: 2218-2226.). One strategy for overcoming this problem is to employ a genetically modified recombinant adenovirus that has an increased MOI (multiplicity of infection) or which can infect cells independently of the receptor. In addition to the genetic manipulation of the adenovirus itself, an external factor, such as a liposome, a cation, a cytopermeable peptide, etc. may be used to form a complex with recombinant adenovirus which can invade irrespective of the expression of CAR.

A great barrier to the gene therapy based on a recombinant adenovirus is a neutralizing antibody (nAb) to adenovirus. Adenoviral infections frequently occur in people, generally without causing serious symptoms. Thus, immune responses to adenoviruses are induced in most people so that they have neutralizing antibodies to adenoviruses. Due to this, recombinant adenoviruses, when injected to deliver a gene, cannot enter target cells, but are removed by neutralization (Clin Diagn Lab Immunol. 2004; 11:351-357). Therefore, a strategy for evading the attack of neutralizing antibodies is required for the application of vaccines and gene therapeutics based on recombinant adenoviruses to have practical use. According to reports to date, encapsulation of adenoviruses with liposomes using lipids such as cholesterols or with (polyethylene glycol) or PLGA (poly lactic-co glycolic acid) makes it possible to avoid the attacks of neutralizing antibodies to some degree (Mol. Ther. 2002; 5:233-241, Gene Ther. 2005; 12:579-587, Gene Ther. 1998; 5:740-746.). However, such single materials cannot encapsulate the whole adenovirus completely, so that infectivity is still decreased by a high concentration of neutralizing antibodies. What is more important, the encapsulation may mask ligands for the adenovirus receptors, resulting in a decrease in the uptake of the virus by the cells that express CAR as well as by the cells that do not express CAR. Therefore, there is a pressing need for the development of a novel adenovirus composite that can compensate for the drawbacks of the encapsulation.

As reported previously, cations such as calcium ($Ca^{2+}$) mitigate electrostatic repulsion between adenoviral capsids and cellular membranes, both being negatively charged, and combine with phosphates to form co-precipitates with adenoviruses, allowing the virus particles to mediate CAR-independent gene delivery (J Clin Invest. 1998; 102:184-193.). In addition, a recent study has reported that the lanthanide elements including lanthanum (Lantanium, ($La^{3+}$) and gadolinium ($Gd^{3+}$), which are trivalent cations, have relatively stronger positive charges per volume and are more effective in mitigating electrostatic repulsion, compared to a calcium ion, which is a divalent anion (Gene Ther. 2008; 15:357-363). However, upon intracellular uptake, the lanthanide elements, which are non-dietary minerals, have the likelihood of interfering with main metabolic reactions such as enzymatic actions or neurotransmission. Hence, it is reluctant and difficult to apply the lanthanide elements to clinical practice.

Iron (Fe) is a transition element with the atomic number 26, which can be a di- or trivalent cation. In the body, iron plays an important role, acting as a main component of hemoglobin, which is responsible for oxygen and carbon dioxide transport. Thus, the biological function of iron is responsible for providing energy to power the functions of the organism. In addition, iron is highly biocompatible with and safe to the body, as proven by its abundance in the body. The iron precipitate ferric phosphate is also not toxic to the body.

However, little study has been done on the use of iron ions in the delivery of viral vectors into cancer cells and stem cells that do not express CAR.

Thus, a novel viral composite that can introduce a viral vector independently of CAR expression and can effectively evade anti-viral neutralizing antibodies is needed.

DISCLOSURE

Technical Problem

Leading to the present invention, intensive and thorough research into effective viral vector-mediated gene delivery, conducted by the present inventors, resulted in the finding that a viral vector, when combined with iron ions, can be effectively transfected into cells in a CAR-independent manner and are able to evade neutralizing antibodies to the viral vector and that even when prepared with a high concentration of iron ions, the composite is low in cytotoxicity and thus safe to the body.

Technical Solution

It is therefore an object of the present invention to provide a method for the intracellular delivery of a viral vector using an iron ion/viral vector composite.

It is another object of the present invention to provide a recombinant viral vaccine composition comprising an iron ion/viral vector composite.

BEST MODE

In accordance with an aspect thereof, the present invention provides a method for viral vector-mediated gene delivery cells, comprising:
1) combining iron ions with a viral vector to form a composite, and
2) incubating and contacting the cells with the iron ion/viral vector composite.

In accordance with another aspect thereof, the present invention provides a recombinant viral vaccine composition, comprising the iron ion/viral vector composite.

Below, a detailed description will be given of the present invention.

In the method for the delivery of a viral vector into cells in accordance with the present invention, an iron ion/viral vector composite is brought into contact with or is incubated with prokaryotic or eukaryotic cells so that the viral vector is delivered into the cytoplasm or nucleus of the prokaryotic or eukaryotic cells.

Preferably, the iron ions may be di- or trivalent.

The viral vector useful in the present invention can carry a gene that can express any biologically functional material responsible for any physiology in the body and may be derived from various viruses including, but not limited to, adenoviruses, vaculoviruses, parvoviruses, semiliki forest viruses, canarypox viruses, vaccinia viruses, fowlpox viruses, sindbis viruses, retroviruses, piconaviruses and, alphaviruses.

The target cells to be recipients of the viral vector are preferably cancer cells or stem cells on which the coxakievirus and adenovirus receptor (CAR) is expressed at a low rate.

Examples of the target cells include rat bone marrow mesenchymal stem cells (rBMSC), a human cervical cell line (HeLa), and a human amelanotic melanoma cell line (A375), all free from the expression of CAR, but are not limited thereto.

As used herein, the term "contact," means that iron ions in the iron ion/viral vector composite are brought into contact with cells in vivo or ex vivo by administration through an intracellular, intraperitoneal, intravenous, oral, intranasal, subcutaneous, intradermal or intramucosal route or by inhalation, whereby the iron ions help the viral vector enter the cytoplasm or nucleus of prokaryotic or eukaryotic cells.

The iron ion/viral vector composite according to the present invention can mediate intracellular gene delivery and expression in a CAR-independent manner and at an increased rate. The effect of iron ions on the gene delivery of the composite is almost the same independent of their oxidation states, that is, ferric and ferrous. Further, iron ions exhibits viral vector-mediated gene delivery at an efficiency 60 times as high as that guaranteed by calcium ions. In addition, the iron ion/viral vector composite according to the present invention can very effectively evade anti-viral neutralizing antibodies, and the extremely low cytotoxicity of iron ions allows the safety of the composite to the body.

Therefore, the iron ion/viral vector composite according to the present invention can be used as an active ingredient of a recombinant viral vaccine composition.

In addition to the active ingredient, the composition of the present invention may further comprise at least one pharmaceutically acceptable carrier. Examples of the pharmaceutically acceptable carrier useful in the present invention include physiological saline, sterile water, Ringer's solution, buffered saline, a dextrose solution, a maltodextrin solution, glycerol, ethanol and a combination thereof. If necessary, a typical additive such as an antioxidant, buffer, a bacteriostatic agent, etc. may be used. Moreover, a diluent, a dispersant, a surfactant, a binder and/or a lubricant may be used to prepare injections, pills, capsules, granules, or tablets from the composition. Further, the composition may be formulated into suitable dosage forms according to disease or ingredient using a method known in the art or disclosed in Remington's Pharmaceutical Science (latest version), Mack Publishing Company, Easton Pa.

According to the purpose, the composition of the present invention may be administered into humans or animals via various routes including parenteral, intraarterial, intradermal, transdermal, intramuscular, intraperitoneal, intravenous, subcutaneous, oral and intranasal routes. The effective dose of the composition is dependent on various factors including the patient's weight, age, sex, general health state and diet, the time and route of administration, excrement rate, and the severity of disease. The composition may be administered in a single dose or it may be spread out over multiple doses per day, with the daily dose ranging from 10 ng/kg to 10 mg/kg and preferably from 80 to 400 ng/kg.

MODE FOR INVENTION

A better understanding of the present invention may be obtained through the following examples which are set forth to illustrate, but are not to be construed as limiting the present invention.

Example 1

Effect of Ferric Irons on the Delivery of Adenoviral Vector into Cells

To examine whether ferric irons ($Fe^{3+}$) improve the delivery of iron vectors into cells, the adenoviral vector rAd/EGFP, which carries a GFP (green fluorescent protein) gene, was employed. First, 30 or 100 MOI of rAd/EGFP was mixed and incubated with 2 μM, 10 μM or 50 μM ferric ions for 30 min at room temperature, followed by infection for 2 hours into rat bone marrow mesenchymal stem cells (rBMSC), the human cervical cancer cell line HeLa, and the human amelanotic melanoma cell line (A375), all free from the expression of CAR, a primary receptor for adenoviruses. Then, the viral mixture was removed and the medium was changed with DMEM before incubation for two days in a $CO_2$ incubator ($CO_2$ water Jacketed Incubator, Form a Scientific™). The cells were detached by trypsinization and analyzed for intracellular GFP level using FACS (fluorescence activated cell sorter, BD).

Figure 1:
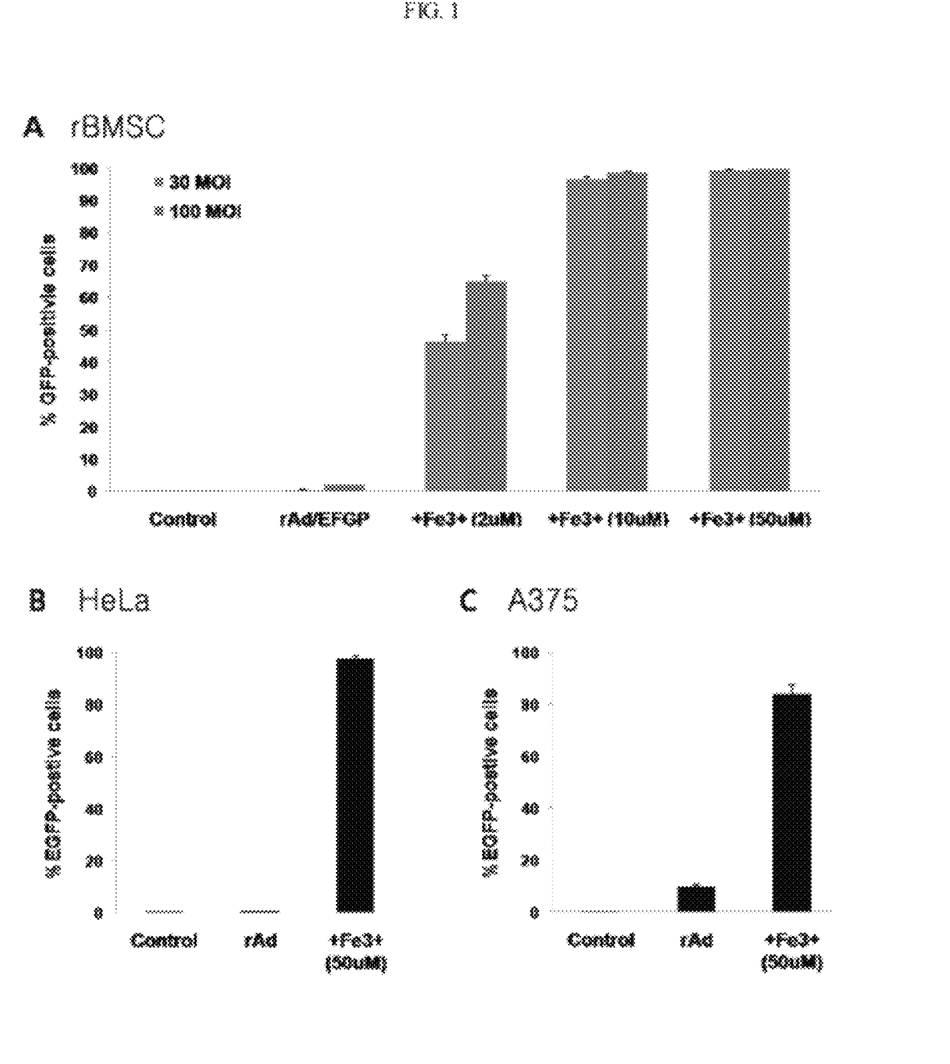
FIG. 1 is of graphs showing GFP levels in rat bone marrow mesenchymal stem cells (rat BMSC), human cervical cells (HeLa), and human amelanotic melanoma cells (A375) treated with a ferric ion/adenoviral vector composite, as determined by FACS (fluorescence activated cell sorter, BD).

The results are shown in FIG. 1.

As can be seen in FIG. 1, when the adenoviral vector alone infected rBMSC, the gene delivery rate was measured to be up to 5% even at 100 MOI as well as 30 MOI, so that almost no GFP gene delivery was achieved. In contrast, the ferric ion/adenoviral vector composite was observed to deliver the GFP gene into rBMSC in an iron dose-dependent manner. Particularly, the adenoviral vector was introduced into the cells at a rate of 95% or higher even when it was used at a concentration of 10 μM. In addition to rBMSC, the human cervical cell line (HeLa) and the human amelanotic melanoma cell line (A375) were observed to increase the intracellular uptake of the adenoviral vector about 150- and 10-fold, respectively, upon treatment with the ferric ion/adenoviral vector composite.

Therefore, the iron ion/adenoviral vector composite according to the present invention can effectively mediate CAR-independent gene delivery into various cells.

Example 2

Comparison of Intracellular Delivery of Adenoviral Vector among Ferrous, Ferric and Calcium Ions Ferrous and ferric ions were compared with calcium ions, known to improve the gene delivery of adenoviral vectors, for efficacy of gene delivery. In this regard, rBMSC was treated with rAd/EGFP (30 MOI) and 50 μM cations ($Fe^{2+}$, $Fe^{3+}$, $Ca^{2+}$) in the same manner as in Example 1, and the efficacy of gene delivery was compared among the cations.

Figure 2:
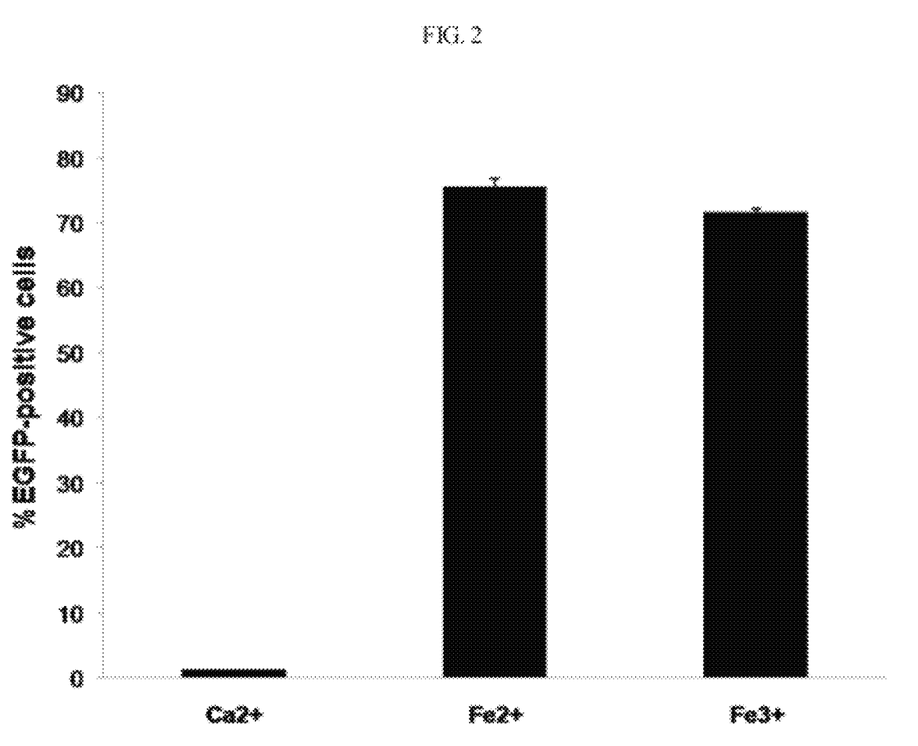
FIG. 2 is a graph showing the efficiency of adenoviral vector-mediated gene delivery in rat BMSC when the adenoviral vector is combined with ferrous or ferric ions ($Fe^{2+}$, $Fe^{3+}$) or calcium ions ($Ca^{2+}$)

The results are shown in FIG. 2.

As is apparent from the data of FIG. 2, ferrous and ferric ions allowed the adenoviral vector to be delivered at similar efficacies, and both showed gene delivery efficiency 60 times as high as that of calcium ions.

Example 3

Ability of Ferric Ions to Evade Adenoviral Vector from Neutralizing Antibody

To examine whether ferric ions interfere with the counteraction of neutralizing antibodies against the intracellular uptake of the viral vector, an adenoviral vector was intramuscularly injected twice into mice at regular intervals of two weeks, after which sera were taken from the mice. 100 MOI of rAd/EGFP was incubated with 50 μM ferric ions at room temperature for 30 min to form a composite (or a precipitate). The immunized sera were diluted 1/16 or 1/256 and added to the composite. Incubation for 30 min allowed the neutralizing antibodies to sufficiently bind to the composite. A group treated with the adenovirus alone was used as a control. After incubation with the sera for 30 min, the viral composite was infected for 2 hours into rBMSC. Forty four hours after infection, gene expression was analyzed using FACS.

Figure 3:
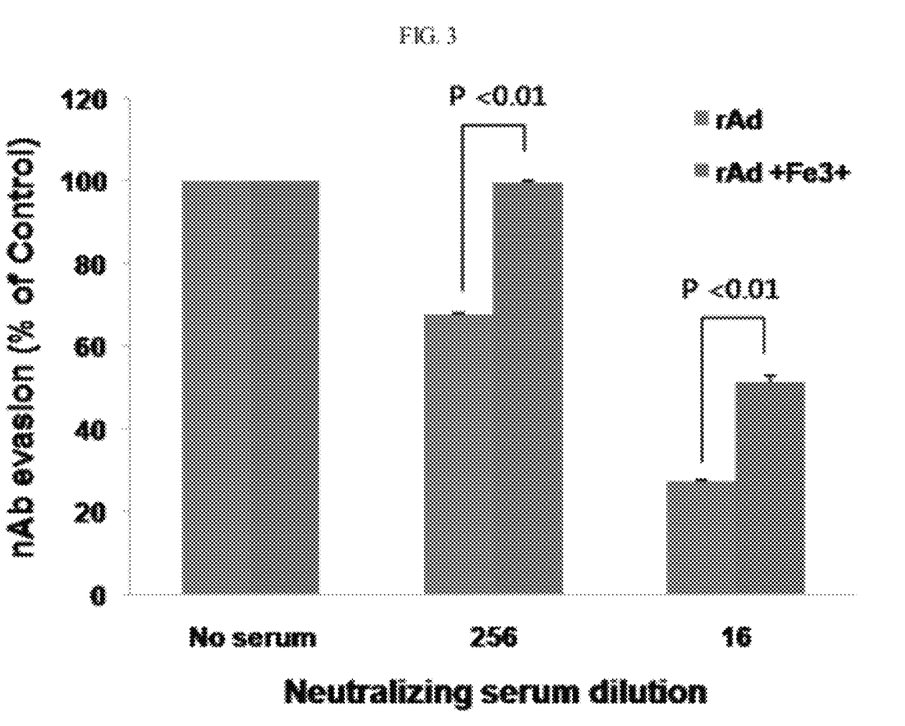
FIG. 3 is a graph showing the ability of ferric ions ($Fe^{3+}$) to spare the adenoviral vector from anti-adenovirus neutralizing antibodies in rat BMSC.

The results are shown in FIG. 3.

As can be seen in FIG. 3, the neutralizing antibody serum decreased the intracellular uptake of the adenoviral vector by as much as 70% when the adenoviral vector was used alone whereas the iron ion/adenoviral vector composite did not decrease in gene delivery against the 1/256-diluted sera at all and guaranteed the intracellular uptake of the adenoviral vector at a rate of 50% even in the presence of a high concentration of neutralizing antibodies (1/16 diluted sera).

Therefore, the iron ion/viral vector composite according to the present invention has excellent ability to evade neutralizing antibodies against adenoviruses.

Example 4

Assay for Cytotoxicity of Ferric Ions

A cytotoxicity assay was done with rBMSC in order to evaluate the safety of ferric ions alone or the ferric ion/adenoviral vector composite to the body. rBMSC was incubated for 2 hours with 0.2 μM~50 mM ferric ions alone or in combination with 100 MOI of an adenoviral vector. On the next day, cell viability was determined using a CCK8 kit (DOJINDO, Japan).

Figure 4:
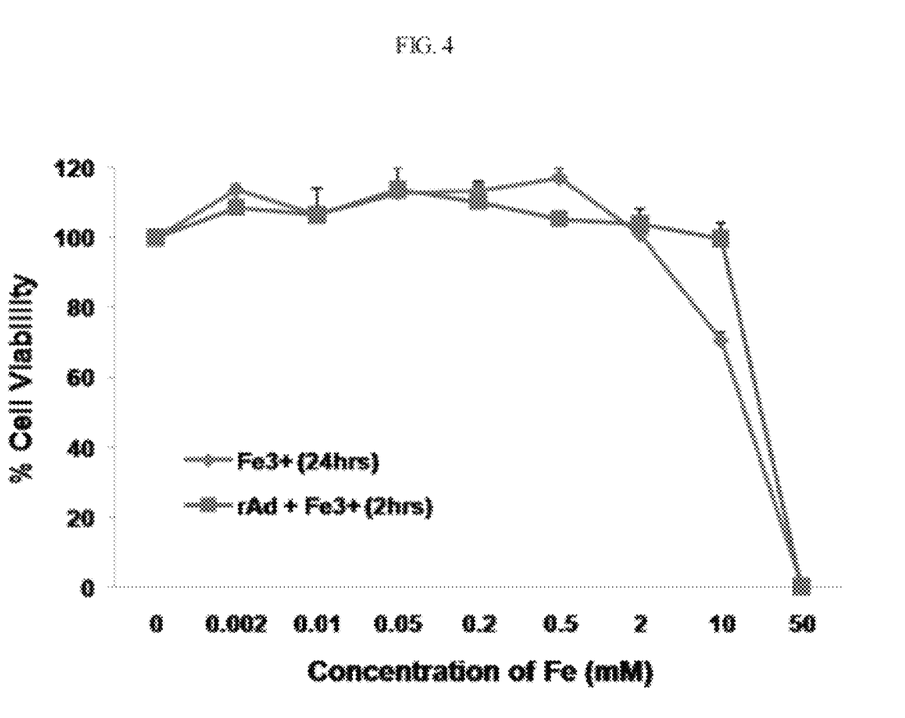
FIG. 4 is a graph showing the cytotoxicity of ferric ions ($Fe^{3+}$) according to concentration (2 µM~50 mM) in rat BMSC treated with ferric ions alone or a ferric ion/adenoviral vector composite.

The results are shown in FIG. 4.

As can be seen from the data of FIG. 4, cell viability was plotted in similar patterns for the ferric ions alone and the ferric ion/adenoviral vector composite. Cytotoxicity was observed to start at an iron ion concentration of 10 mM and the cell viability was decreased to zero at an iron ion concentration of 50 mM. Hence, the concentration of ferric ions that causes 50% cell viability is between 10 and 50 mM, which is 1000-fold higher than 10~50 μM, the iron ion concentration used for gene delivery in practice. Accordingly, the method for the delivery of adenoviral vectors using iron ions at such a concentration in accordance with the present invention is safe without incurring cytotoxicity.

Example 5

Effect of Ferric Ions on In vivo Delivery of Adenoviral Vector

To examine whether iron ions improve adenoviral vector-mediated gene delivery and gene expression in vivo, a recombinant adenoviral vector carrying a brain-derived neurotrophic factor (BDNF) gene (rAd/BDNF) was employed because the factor is detectable in the blood. To C57BL/6 mice, $5 \times 10^6$ pfu of the adenoviral vector or a composite comprising $5 \times 10^6$ pfu of the adenoviral vector and 50 μM or 200 μM ferric ions was intramuscularly injected. Twenty four hours after injection, blood was taken from the mice and subjected to ELISA analysis to determine blood BDNF levels.

Figure 5:
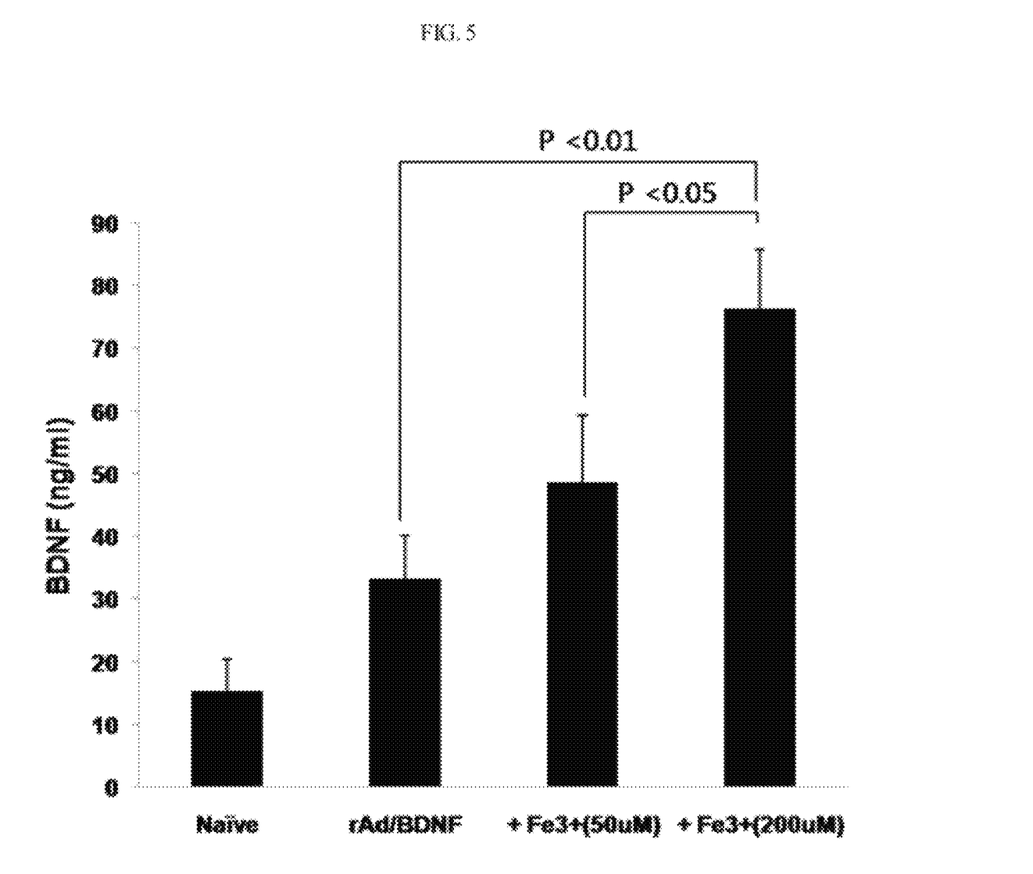
FIG. 5 is a graph showing blood BDNF levels in C57BL/6 mice injected with ferric ions ($Fe^{3+}$) alone or a ferric ion/adenoviral vector composite, as measured by ELISA.

The results are shown in FIG. 5.

As is apparent from the data of FIG. 5, higher blood BDNF levels were detected in the mice treated with the ferric ion/adenoviral vector composites than with the adenoviral vector alone. Therefore, the iron ion/adenoviral vector composites according to the present invention exhibits increased gene delivery and gene expression rates.

INDUSTRIAL APPLICABILITY

As described hitherto, the iron ion/viral vector composite according to the present invention can mediate intracellular gene delivery and expression in a CAR-independent manner at a high efficiency thanks in part to its ability to evade neutralizing antibodies. Further, the composite is safe to the body as it exhibits low cytotoxicity even at a high concentration of iron ions.

We claim:

1. A method for viral vector-mediated gene delivery into cells employing iron ion/viral vector composite, comprising:
   1) combining an iron ion solution with a viral vector to form a composite; and
   2) incubating and contacting the cells with the iron ion/viral vector composite, wherein the concentration of the iron ion in the solution is in the range of 2-200 µM; and
   wherein transfection of the iron ion/viral vector composite into cells is not dependent on expression of a Coxsackievirus and Adenovirus Receptor (CAR).

2. The method of claim 1, wherein the iron ions are ferrous or ferric ions.

3. The method of claim 1, wherein the viral vector is selected from the group consisting of an adenoviral vector, a vaculoviral vector, a parvoviral vector, a semiliki forest viral vector, a canarypox viral vector, a vaccinia viral vector, a fowlpox viral vector, a sindbis viral vector, a retroviral vector, a piconaviral vector, and an alphaviral vector.

4. The method of claim 1, wherein the cells are cancer cells or stem cells which have a low expression level of a Coxsackievirus and Adenovirus Receptor (CAR).

5. The method of claim 1, wherein the cells are incubated for 0.5-2 hours in step 2).

* * * * *